United States Patent [19]

Berge et al.

[11] 4,374,755

[45] Feb. 22, 1983

[54] MAGNESIUM DISILOXIDE COMPOUNDS

[75] Inventors: Charles T. Berge; Mark P. Mack; Charles M. Starks, all of Ponca City, Okla.

[73] Assignee: Conoco Inc., Ponca City, Okla.

[21] Appl. No.: 277,583

[22] Filed: Jun. 26, 1981

[51] Int. Cl.$^3$ .......................... C07F 7/04; C07F 7/08; B01J 31/12
[52] U.S. Cl. ................................. 252/431 R; 556/463
[58] Field of Search ..................... 752/431 R; 556/463

[56] References Cited

U.S. PATENT DOCUMENTS 2,762,825  9/1956  Kautsky et al. ............... 556/463 X

*Primary Examiner*—Paul F. Shaver
*Attorney, Agent, or Firm*—Cortlan R. Schupbach, Jr.

[57] ABSTRACT

Novel magnesium disiloxide compounds and methods for their preparation are disclosed. The magnesium disiloxides so obtained are useful starting materials for the preparation of active catalysts for olefin polymerizations.

12 Claims, No Drawings

MAGNESIUM DISILOXIDE COMPOUNDS

MAGNESIUM DISILOXIDE COMPOUNDS

This invention relates to novel magnesium disiloxide compounds. More particularly, this invention relates to the preparation of novel magnesium disiloxide compounds by several methods. The disiloxides so obtained are useful starting materials for the preparation of active catalysts for olefin polymerizations.

Silicon-containing materials such as silanes and silanols are known in the art. However, no art is known which teaches the noval magnesium disiloxide materials of the present invention. Representative but non-exhaustive examples of silicon-containing materials can be found in U.S. Pat. Nos. 3,166,542; 3,205,177; 3,166,542; and 4,238,354. Other references representative but non-exhaustive of the art include Japan Kokai Pat. Nos. 7605385; 7697687; 7970387; and 78136087. These references generally teach that polymerization catalysts for olefin polymerization can be made utilizing silane or siloxide compounds as intermediates. However, none of these references teach or suggest that disiloxides can be obtained, which materials are active ingredients in the preparation of highly active catalysts for the polymerization of olefins.

It would be of great value to provide novel magnesium disiloxide compounds which are useful as starting materials for catalysts for olefin polymerization.

It is therefore an object of the present invention to provide novel magnesium disiloxide compounds and methods for their preparation. Other objects will become apparent to those skilled in this art as the description proceeds.

We have now discovered novel magnesium disiloxide compounds of the general formula

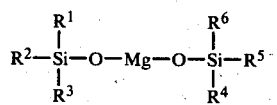

wherein $R^1$, $R^2$, $R^3$, $R^4$, $R^5$ and $R^6$ are, independently, hydrogen, alkyl groups, cycloalkyl groups, alkaryl groups, aralkyl groups, aryl groups or bicycloalkyl groups containing from 1 to 20 carbon atoms.

Representative but non-exhaustive examples of the magnesium disiloxides encompassed within the present invention are those having the formulas:

$(CH_3)_3Si-O-Mg-O-Si(CH_3)_3$,
$(C_2H_5)_3Si-O-Mg-O-Si(C_2H_5)_3$,
$(n-C_4H_9)(C_6H_5)(CH_3)Si-O-Mg-O-Si(CH_3)(C_6H_5)(n-C_4H_9)$;
$(n-C_5H_{11})(cycloC_6H_{11})(CH_3)Si-O-Mg-O-Si(CH_3)(cycloC_6H_{11})(n-C_5H_{11})$,
$(C_{10}H_{21})(n-C_4H_9)HSi-O-Mg-O-SiH(n-C_4H_9)(C_{10}H_{21})$,
$(C_{14}H_{29})(CH_3)HSi-O-Mg-O-SiH(CH_3)(C_{14}H_{29})$,
$(n-C_{20}H_{41})(i-C_4H_9)HSi-O-Mg-O-SiH(i-C_4H_9)(n-C_{20}H_{41})$,
$(p-CH_3C_6H_4)(CH_3)(C_2H_5)Si-O-Mg-O-Si(C_2H_5)(CH_3)(p-CH_3C_6H_4)$,
$(C_6H_5C_2H_4)(C_2H_5)_2Si-O-Mg-O-Si(C_2H_5)_2(C_6H_5C_2H_4)$.

The novel magnesium disiloxides of the present invention can be prepared by any one of several methods.

One method comprises contacting a silanol of the general formula

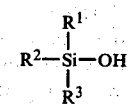

with magnesium metal in an inert solvent to initiate a reaction, allowing the reaction to occur, and then recovering the magnesium disiloxide wherein $R^1$, $R^2$, and $R^3$ are, independently, hydrogen, alkyl groups, cycloalkyl groups alkaryl groups, aralkyl groups, aryl groups or bicycloalkyl groups containing from 1 to 20 carbon atoms.

Likewise these materials may be prepared by contacting a silanol of the general formula

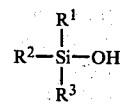

with a magnesium compound of the general formula $R^7-Mg-R^8$ in an inert solvent to initiate a reaction, allowing the reaction to occur, and recovering the magnesium disiloxide wherein $R^1$, $R^2$, and $R^3$ are, independently, hydrogen, alkyl groups, cycloalkyl groups, alkaryl groups, aralkyl groups, aryl groups or bicycloalkyl groups containing from 1 to 20 carbon atoms, and $R^7$ and $R^8$ are, independently, hydrogen, alkyl groups, alkaryl groups, aralkyl groups, aryl groups and cycloalkyl groups containing from 1 to 20 carbon atoms.

A third method of preparing the novel magnesium disiloxide of the present invention comprises contacting a silyl halide of the general formula

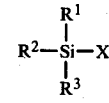

wherein X is Cl, Br or I with magnesium hydroxide in an inert solvent to initiate a reaction, allowing the reaction to occur, and recovering the magnesium disiloxide wherein $R^1$, $R^2$, and $R^3$ are independently, hydrogen, alkyl groups, cycloalkyl groups, alkaryl groups, aralkyl groups, aryl groups or bicycloalkyl groups containing from 1 to 20 carbon atoms.

This reaction forms an acid of the formula HX, which optionally but not critically can be neutralized with a base. Representative but non-exhaustive examples of suitable bases are pyridine, triethylamine and ammonia.

A fourth method of preparing the novel magnesium disiloxides of the present invention comprises contacting a silanolate of the general formula

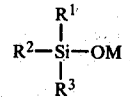

with a magnesium halide in an inert solvent to initiate a reaction, allowing the reaction to occur, then recovering the magnesium disiloxides of the present invention therefrom, wherein $R^1$, $R^2$ and $R^3$ are, independently, hydrogen, alkyl groups, cycloalkyl groups, alkaryl groups, aralkyl groups aryl groups or bicycloalkyl groups containing from 1 to 20 carbon atoms and wherein M is selected from the group consisting of sodium, potassium and lithium. Magnesium metal can be used in admixture with magnesium halides.

A fifth method of preparing the novel magnesium disiloxide of the present invention comprises contacting a silating agent of general formula

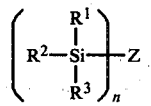

with a magnesium hydroxide in an inert solvent to initiate a reaction, allowing the reaction to occur, then recovering the magnesium disiloxide of the present invention therefrom wherein n is 1 or 2 and $R^1$, $R^2$, and $R^3$ are, independently, hydrogen, alkyl groups, cycloalkyl groups, alkaryl groups, aralkyl groups, aryl groups or bicycloalkyl groups containing from 1 to 20 carbon atoms, and wherein when n=1, Z is a structure selected from the group consisting of

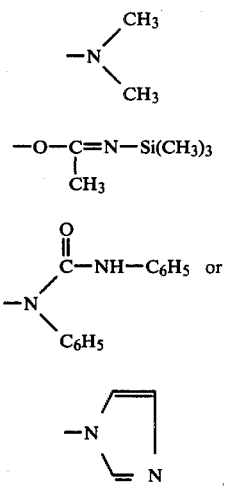

and when n=2, Z is a structure selected from the group consisting of

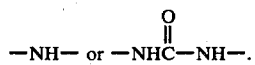

Optionally, but not critically, a reaction catalyst can be used to facilitate the reaction. Representative but non-exhaustive examples of such catalysts are aluminas and Me$_3$SiCl.

Normally, the reactions described above are carried out in similar temperature ranges which range from about −20° C. to about 100° C. for sufficient time for reaction to occur. It is more preferred to carry out these reactions at temperatures of from about 20° C. to about 75° C. for a time sufficient for the reactions to occur.

Pressure or lack of pressure does not appear to be detrimental to the instant invention, although at extremely high pressures the reaction can be made to proceed more quickly. It is likewise preferred that the materials used in the reaction be as pure as reasonably possible, although it is apparent that impurities which do not actively enter into the reaction and substitute for the reactants are not detrimental in small amounts.

Representative but nonexhaustive examples of inert solvents which can be utilized in the method of the present invention to obtain magnesium disiloxides are saturated alkanes, both branched and straight chain, cycloalkanes, benzene, toluene, xylenes, tetrahydrofuran, and ethyl ether.

Analogues of the above hydrocarbons or their mixtures can be used; for example, LPA solvent (low polynuclear aromatic solvent, a very high purity aliphatic hydrocarbon having a molecular weight very similar to kerosene and a low aromatic and olefin content, sold by Conoco Inc.).

However obtained, the magnesium disiloxides of the present invention are starting materials for the preparation of supported olefin polymerization catalysts. It is known that in the preparation of supported catalysts, especially Zeigler/Natta catalysts, the transition metal halide is often reduced by a metal, metal alkyl, or metal alkyl halide in the presence of a support. In some cases the reducing agent becomes the support material when oxidized by reaction with a transition metal. The use of mild reducing agents in an effort to minimize overreduction of the transition metal to an oxidation state which is less active in catalytic polymerization is also known.

It is also known to use a silicon-containing support for magnesium compounds and titanium tetrachloride in the preparation of such catalysts. Most of these silicon-containing materials are silanols or siloxides, which in the presence of a reducing agent and titanium in an oxidation state of 4+ results in the reduction of titanium, to an oxidation state of 3+ producing an active polymerization catalyst.

In using the materials of the present invention in the preparation of olefin polymerization catalysts, the magnesium disiloxides of the present invention are added to a hydrocarbon solution containing a transition metal such as titanium tetrachloride. A reaction occurs, and after removal of soluble components a solid material is obtained which is useful as a polymerization catalyst. Normally, anhydrous materials are used in such preparations.

Any transition metal of the groups 4b to 8 in the periodic chart (CRC Handbook of Chemistry and Physics, 58B Ed, 1977) can be used in the preparation of catalysts using the process of the present invention. Representative but non exhaustive examples of specific transition metal compounds which are useful are TiCl$_4$, VCl$_5$, VOCl$_3$, CrCl$_2$ and TiCl$_2$ (cyclopentadiene)$_2$.

Any solvent which remains relatively unreactive in the catalyst synthesis process can be used. Saturated hydrocarbons such as the alkanes will be most common, although mixtures of materials can be used such as low polynuclear aromatic solvents and raffinate solvents.

The invention is more concretely described with reference to the examples below wherein all parts and percentages are by weight unless otherwise specified. The examples are provided to illustrate the present invention and not to limit it.

Examples 1 through 4 illustrate general procedures for the preparation and isolation of magnesium disiloxides using the process of the present invention.

EXAMPLE 1

Magala BEM, 0.0362 moles (n-butylethylmagnesium) in heptane, trademark of and sold by Texas Alkyls Co.

was placed in a dry 500 milliliter (ml) round bottom flask and purged with argon to exclude oxygen. Triethylsilanol (0.0736 moles), as a neat liquid, was added to the heptane solution of butylethylmagnesium over a time of 10 minutes. Substantial foaming was observed with evolution of gas. After the gas evolution subsided the mixture was heated to reflux (60° C.) for 2 hours. The reaction mixture was then cooled to 25° C. while maintaining an inert atmosphere. A white material was formed during the reaction and much of the solvent was contained in the precipitated mass.

The entire sample was centrifuged for 10 minutes at 2500 rpm. The liquid was removed. Dry, oxygen-free hexane was added (200 ml) and the solid stirred with the hexane for 15 minutes. This cycle of centrifuge-wash-centrifuge was repeated three times to insure removal of unreacted starting materials.

The final hexane slurry was evaporated to dryness on laboratory vacuum at 25° C. to give the solid bis(triethylsiloxy) magnesium. The sample was exposed to full vacuum (<10 micron) and heated to 45° C. for 1 hour to insure thorough solvent removal. Hydrolysis of a portion of the solid, with aqueous HCl and subsequent analysis for gas above the aqueous phase, indicated no ethane or butane present.

EXAMPLE 2

Magnesium powder (0.0500 moles; −200 to +325 mesh) is placed in a 500 ml round-bottom flask fitted with a sidearm filter made of fritted glass. The flask was purged thoroughly with argon. Freshly distilled tetrahydrofuran (THF), free of both water and oxygen, is placed in the flask under an argon atmosphere. Triethylsilanol (0.110 moles), as a neat liquid, is added over 20 minutes to the flask. The reaction is stirred at 25° C. for 2 hours, then refluxed for an additional 2 hours. The hot THF solution is filtered into a dry-oxygen free flask. The residue is washed with hot THF, then three times with 200 ml room temperature THF and filtered into a dry, oxygen-free flask. The filtrate is evaporated under vacuum to give magnesium disiloxides as a white solid which is washed thoroughly with dry, oxygen-free hexane to remove all unreacted silanol.

EXAMPLE 3

Magnesium hydroxide (0.0989 moles) is added to a dry 250 ml flask equipped with a reflux condenser. Freshly distilled tetrahydrofuran (THF) is then added (125 ml) to the flask under an argon atmosphere. Hexamethyldisilazane (0.0989 moles) is added followed by approximately 20 milligrams (mg) γ-alumina. The reaction mixture is allowed to reflux for 4 hours and thereafter is cooled to 25° C. An argon atmosphere is maintained throughout the reaction. The THF is removed by distillation until a liquid volume of one fourth that of the original reaction volume is obtained. The slurry is filtered and the solid residue is washed with dry, oxygen-free hexane to remove all traces of unreacted silating agent. Following the final filtration of the hexane wash, the magnesium disiloxide product is extracted from the unreacted magnesium hydroxide using THF as an extraction agent while following standard extraction procedures.

EXAMPLE 4

Anhydrous magnesium chloride (0.050 moles) is placed in a thoroughly dry 500 ml flask and thoroughly purged with argon. Dry-oxygen free tetrahydrofuran (200 ml) is added to the flask under an inert atmosphere. Solid potassium trimethylsilanolate (0.105 moles) is added to the magnesium chloride/THF solution over a 5 minute period to form a reaction mixture. The reaction mixture is heated to reflux for 3 hours, then cooled to 25° C. An argon atmosphere is maintained throughout the reaction. The reaction product is filtered to yield a solid residue. The solid magnesium disiloxide residue is extracted using THF as an extraction agent while following standard extraction procedures.

Example 5 shows the process of the present invention integrated into a method for the preparation of an olefin polymerization catalyst wherein the magnesium disiloxide is not isolated prior to preparing the catalyst.

EXAMPLE 5

One hundred milliliters (ml) of oxygen-free dry normal hexane was added under anhydrous conditions to a dry centrifuge tube containing 6.8312 grams of a composite material having the following composition: magnesium chloride (90.7% by weight), $Mg^o$ (6.7% by weight) and magnesium oxide (2.6% by weight). Two equivalents (38.04 millimoles) of triethyl silanol in 15 ml hexane was then added to a centrifuge tube while maintaining a temperature of 25.5° C. over a 2 hour period. The resulting mixture was stirred at 25.5° C. for 18 hours, at which time the slurry had thickened to form a gelatinous material containing magnesium disiloxide. The gelatinous slurry was cooled to −10° C. and transferred over a 3 hour period to a second centrifuge tube containing 6.5585 grams $TiCl_4$ in 30 ml of oxygen-free dry normal hexane. The $TiCl_4$/hexane solution was kept at −10° C. during the slurry transfer. The resulting slurry was centrifuged for 10 minutes at −5° C., after which time the supernate was removed to yield a solid. Two hundred ml of hexane was added to the solid and the resulting slurry stirred for an additional 10 minutes at −5° C. The washing procedure was repeated 3 times. The resulting solid was slurried with 200 ml of oxygen-free dry hexane and standardized for titanium per volume. The slurried solid was utilized as a polymerization catalyst.

EXAMPLE 6

The recovered solid of Example 5 was utilized in the polymerization of 1-butane using 3.75 ml of a 24.7% by weight triethylaluminum co-catalyst in heptane. Polymerization was carried out by placing the catalyst and co-catalyst in liquid monomer at 60° C. for 40 minutes. The polymerization produced 116.6 grams of poly(1-butene) to give an activity of 52.6 kilograms of polymer per gram of titanium per hour.

EXAMPLE 7

The recovered solid of Example 5 was utilized in the polymerization of ethylene using a triethylaluminum as a co-catalyst (0.74 ml; 24.7% in heptane). The polymerization was conducted in hexane diluent (500 ml) with 120 pounds per square inch gauge (psig) ethylene pressure at 85° C. for 60 minutes. The catalyst contained 0.30 mg Ti and produced 18.2 gram polyethylene. Catalyst activity was 60.7 kg polymer per gram titanium per hour.

EXAMPLE 8

Bis(triethylsiloxy) magnesium (0.050 moles) prepared as described in Example 1 is added to anhydrous magnesium chloride (0.050 moles) in oxygen-free dry toluene (200 ml) at 25° C. The reaction mixture is stirred for 5 hours, then cooled to −10° C. The reaction solution is transferred over a 3 hour period to a centrifuge tube containing 1.000 grams TiCl$_4$ and 20 ml of oxygen-free dry toluene. The TiCl$_4$/toluene solution is maintained at −10° C. during the transfer. The resulting slurry is centrifuged for 10 minutes at a temperature of −5° C. The supernate is removed. One hundred ml of hexane is added and the resulting slurry stirred for 10 minutes. The washing procedure is repeated 3 times. The resulting solid is slurried with 100 ml of oxygen-free dry toluene and standardized for titanium per volume. The solid is recovered from toluene by filtration. The recovered solid is utilized as a polymerization catalyst.

The composition of the Example 1 product was analyzed using atomic absorption for Magnesium determination and Carbon/Hydrogen analysis was made using a Perkin-Elmer 240 elemental analyzer. The theoretical ratio of Mg/C/H is 1/12/30 respectively. The analysis showed an actual ratio of 1/11.9/29.5.

A 292.5 milligram sample of the Example 1 product was decomposed with aqueous HCl in a closed vessel. Gas chromatographic analysis of the off-gas showed substantially no butane or ethane present indicating the absence of n-butylethylmagnesium or triethylsiloxybutyl (or ethyl) magnesium.

A substituent-sensitive nuclear magnetic resonance (NMR) test for silicon 29 was carried out. The Example 1 material was shown to be substantially different in chemical shift than the other silicon materials potentially present, where PPM is a frequency absorption shift based on (CH$_3$)$_4$Si standard.

| Compound Formula | Chemical Shift |
| --- | --- |
| (CH$_3$)$_4$Si | 0.0 PPM |
| (CH$_3$CH$_2$)$_3$SiOH | 15.70 PPM |
| [(CH$_3$CH$_2$)$_3$Si]$_2$O | 8.92 PPM |
| [(CH$_3$CH$_2$)$_3$SiO]$_2$Mg | 13.18 PPM |

A differential scanning calorimeter recorded an endotherm centered at 230° C. for the example product. No exotherm was noted on cooling, indicating a decomposition point as opposed to a melting point.

Thus the present invention provides a novel magnesium disiloxide materials as well as a novel method of preparing these materials. These materials are then used as precursors in the preparation of active olefin polymerization catalysts.

While certain embodiments and details have been shown for the purpose of illustrating this invention, it will be apparent to those skilled in this art that various changes and modifications may be made herein without departing from the spirit or scope of the invention.

We claim:

1. A method of preparing a magnesium disiloxide of the general formula

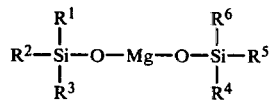

by contacting a silanol of the general formula

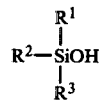

with magnesium metal in an inert solvent, allowing reaction to occur, then recovering magnesium disiloxide, wherein R$^1$, R$^2$, R$^3$, R$^4$, R$^5$, and R$^6$ are, independently, hydrogen, alkyl groups, cycloalkyl groups, alkaryl groups, aralkyl groups, aryl groups or bicycloalkyl groups.

2. A method of preparing a magnesium disiloxide of the general formula

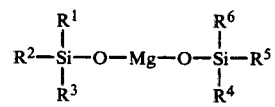

by contacting a silanol of the general formula

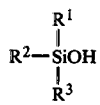

with a magnesium compound of the general formula R$^7$—Mg R$^8$ in an inert solvent, allowing reaction to occur, then recovering magnesium disiloxide, wherein R$^1$, R$^2$, R$^3$, R$^4$, R$^5$, R$^6$, R$^7$, and R$^8$ are, independently, hydrogen, alkyl groups, cycloalkyl groups, aralkyl groups, aryl groups or bicycloalkyl groups each containing from 1 to 20 carbon atoms.

3. A method of preparing a magnesium disiloxide of the general formula

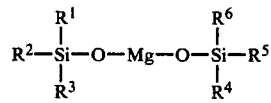

by contacting a silyl chloride of the general formula

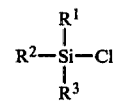

with magnesium hydroxide in an inert solvent to initiate a reaction, allowing the reaction to occur, then recovering magnesium disiloxide, wherein R$^1$, R$^2$, R$^3$, R$^4$, R$^5$, and R$^6$ are, independently, hydrogen, alkyl groups, cycloalkyl groups, aralkyl groups, aryl groups of bicycloalkyl each containing from 1 to 20 carbon atoms or hydride.

4. A method of preparing a magnesium disiloxide of the general formula

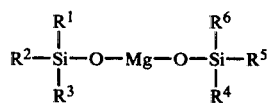

by contacting a silating agent of general formula

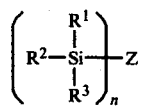

with magnesium hydroxide in an inert solvent to initiate a reaction, allowing the reaction to occur, then recovering the magnesium disiloxide, wherein n is 1 or 2 and where $R^1$, $R^2$, $R^3$, $R^4$, $R^5$, and $R^6$ are, independently, hydrogen, alkyl groups, cycloalkyl groups, alkaryl groups, aralkyl groups, aryl groups or bicycloalkyl groups, and wherein when n=1, Z is selected from the group consisting of

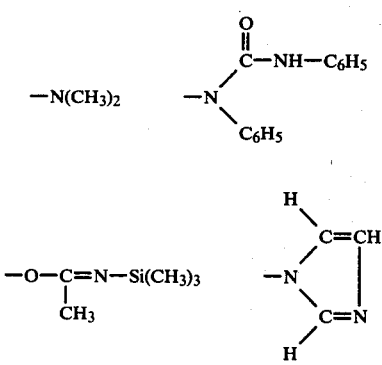

and when n=2, Z is selected from the group consisting of

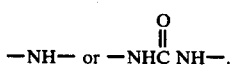

5. A method of preparing a magnesium disiloxide of the general formula

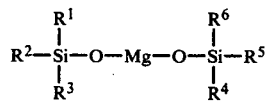

by contacting a silanate of the general formula

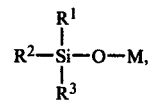

where M is a Group I metal, with at least one magnesium halide in an inert solvent to initiate a reaction, allowing the reaction to occur, then recovering magnesium disiloxide, wherein $R^1$, $R^2$, $R^3$, $R^4$, $R^5$, and $R^6$ are, independently, hydrogen, alkyl groups, cycloalkyl groups, aralkyl groups, aryl groups or bicycloalkyl groups each containing from 1 to 20 carbon atoms.

6. A method as described in claim 5 wherein $R^1$, $R^2$, $R^3$, $R^4$, $R^5$, and $R^6$ are alkyl groups containing from 1 to 4 carbon atoms.

7. A method as described in claim 6 wherein a mixture of magnesium and $MgX_2$ is contacted with a silanol, wherein X is selected from the group consisting of chlorine, bromine, and iodine.

8. A method as described in claim 7 wherein $TiCl_4$ is contacted with the reaction product of magnesium and $MgX_2$ mixture and silanol to form a polymerization catalyst.

9. A method as described in claim 7 wherein the inert hydrocarbon diluent is a saturated hydrocarbon.

10. A method as described in claim 8 wherein the inert hydrocarbon diluent is selected from the group consisting of n-hexane, n-heptane, n-octane, toluene, benzene, xylenes.

11. A method as described in claim 10 wherein the reaction is allowed to proceed at temperatures of from about −20° C. to about 100° C.

12. A catalyst prepared by
(a) placing magnesium disiloxides of the general formula

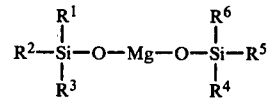

in contact with at least one material selected from the group consisting of Mg and $MgX_2$ in an inert hydrocarbon diluent;

(b) adding a Group 4b to Group 8 transition metal compound to form a solid precipitate, then;

(c) recovering the solid precipitate as a catalyst wherein $R^1$, $R^2$, $R^3$, $R^4$, $R^5$, and $R^6$ are, independently hydrogen, alkyl groups, aralkyl groups, alkaryl groups, cycloalkyl groups, aryl groups or bicycloalkyl groups containing from 1 to 20 carbon atoms, and wherein X is chlorine, bromine or iodine.

* * * * *